(12) United States Patent
Pasha et al.

(10) Patent No.: US 7,335,644 B2
(45) Date of Patent: Feb. 26, 2008

(54) ANTI-HYPERTENSIVE MOLECULES AND PROCESS FOR PREPARATION THEREOF

(75) Inventors: Santosh Pasha, New Delhi (IN); Qadar Pasha, New Delhi (IN); Kashif Hanif, New Delhi (IN); Mahesh Chand Pavar, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 39 days.

(21) Appl. No.: 10/812,831

(22) Filed: Mar. 30, 2004

(65) Prior Publication Data

US 2005/0032709 A1   Feb. 10, 2005

Related U.S. Application Data

(60) Provisional application No. 60/459,143, filed on Mar. 31, 2003.

(51) Int. Cl.
| | |
|---|---|
| A61K 38/06 | (2006.01) |
| A61K 38/05 | (2006.01) |
| C07K 5/08 | (2006.01) |
| C07K 5/02 | (2006.01) |
| C07K 1/00 | (2006.01) |
| C07K 1/14 | (2006.01) |
| C07K 1/04 | (2006.01) |

(52) U.S. Cl. .............. 514/18; 514/2; 514/19; 530/300; 530/331; 530/332; 530/333; 530/344

(58) Field of Classification Search ............ None
See application file for complete search history.

(56) References Cited

U.S. PATENT DOCUMENTS

| | | | | |
|---|---|---|---|---|
| 3,832,337 A | * | 8/1974 | Ondetti et al. | ............ 530/327 |
| 4,687,840 A | | 8/1987 | Pang et al. | |
| 5,440,016 A | * | 8/1995 | Blondelle et al. | .......... 530/330 |
| 5,637,454 A | * | 6/1997 | Harley | ......................... 435/5 |
| 5,698,673 A | * | 12/1997 | Blondelle et al. | .......... 530/329 |
| 6,462,171 B1 | | 10/2002 | Soto-Jara et al. | |
| 7,202,279 B1 | * | 4/2007 | Kozikowski et al. | ........ 514/659 |

FOREIGN PATENT DOCUMENTS

| | | | |
|---|---|---|---|
| GB | 2144128 A | * | 2/1985 |
| JP | 07227281 | | 8/1995 |
| JP | 09169797 | | 6/1997 |
| WO | 01/68114 | | 9/2001 |

OTHER PUBLICATIONS

J. Med. Chem. (1972) 15(5), pp. 479-482.*
Bala, Manju et al. "Novel Peptidomimics as Angiotensin-Converting Enzyme Inhibitors: A Combinatorial Approach", *Bioorganic & Medicinal Chemistry*, vol. 10, (2002), 3685-3691.
English language abstract of JP 09169797, dated Jun. 30, 1997.
English language abstract of JP 07227281, dated Aug. 29, 1995.
Nakamura, Yoshikazu and Koichi Ito. "Making sense of mimic in translation termination", *TRENDS in Biochemical Sciences*, vol. 28(2), (2003), pp. 99-105.
Abstract of Maruyama, S. et al. "Angiotensin I-Converting Enzyme Inhibitory Activity of the Carboxyl-Terminal Hexapeptide of Alpha-S-1 Casein", *Report of the Fermentation Researach Institute*, No. 72, (1989), pp. 25-32.
Abstract of O'Connor B. et al. "Post-Proline Dipeptidylaminopeptidase from Synaptosomal Membranes of Guinea-pig Brain . . . ", *European Journal of Biochemistry*, vol. 154 (2), (1986), pp. 329-336.

* cited by examiner

*Primary Examiner*—Andrew D. Kosar
(74) *Attorney, Agent, or Firm*—Ladas and Parry LLP (57) ABSTRACT

The present invention relates to novel anti-hypertensive molecules. The present invention also provides a process for the preparation of novel antihypertensive molecules. The present invention particularly relates to the preparation of novel Angiotensin Converting Enzyme Inhibitors (ACEI) with prolonged activity. ACE inhibitors play an important role in Renin-Angiotensin-Aldosteron system (RAAS) by inhibiting the activity of Angiotensin Converting Enzyme (ACE) and therefore are used to regulate blood pressure. ACE inhibitors synthesized by the process of present invention have a peptide moiety and nonpeptide moiety. ACE inhibitors, synthesized by this present invention, show enhanced bioavailability and fewer side effects.

11 Claims, 6 Drawing Sheets

Figure 1: Role of Angiotensin Converting Enzyme in RAAS and KKP

Figure 2: Interaction of Ang I with the active site of angiotensin converting enzyme Fig 3: Proposed interactions of designed peptidomimics with the active site of Angiotensin - converting enzyme Figure 4 : Lineweaverburk plot for L-Abrine-Ornithine-Proline. IC50 of L-Abrine-Ornithine-Proline was found to be 10µM.

Figure 5: Tail systolic pressure (TSP) in experimental and control group. Increments in TSP values for methylprednisolone induced experimental group was significantly different after 1st week ($p<0.05$) and 2nd week ($p<0.05$)

Figure 6: Variation in blood pressure measured during i.v. administration of L-Abrine-Ornithine-Proline at doses of 5 mg/kg, 8 mg/kg and 10 mg/kg. Fall of blood pressure at all doses was significant ($p<0.05$).

ANTI-HYPERTENSIVE MOLECULES AND PROCESS FOR PREPARATION THEREOF

This application claims the benefit of U.S. Provisional Application No. 60/459,143 filed Mar. 31, 2003 and incorporates the same by reference.

FIELD OF THE INVENTION

The present invention relates to novel anti-hypertensive molecules. The present invention also provides a process for the preparation of novel antihypertensive molecules. The present invention particularly relates to the preparation of novel Angiotensin Converting Enzyme Inhibitors (ACEI) with prolonged activity. ACE inhibitors play an important role in Renin-Angiotensin-Aldosteron system (RAAS) by inhibiting the activity of Angiotensin Converting Enzyme (ACE) and therefore are used to regulate blood pressure. ACE inhibitors synthesized by the process of present invention have a peptide moiety and nonpeptide moiety. ACE inhibitors, synthesized by this present invention, show enhanced bioavailability and fewer side effects.

BACKGROUND OF THE INVENTION

Hypertension has assumed the form of a grave problem all over the world. In US 23% people are suffering from hypertension. Over three-quarters of women aged 75 or over and 64% of men aged 75 or over have hypertension. (Health, United States, 2002, Table 68). Annually, hypertension cause 23,761 deaths and there are 8.6 deaths per 100,000 population in 2000 (National Vital Statistics Report, Vol. 50, No. 15).

In India, it has been estimated that 10-20% people suffer from hypertension and with increasing urbanization, problem is compounding. Even in India, According to analysis, the prevalence of Hypertension among adults in India is 11%. There is increasing trend in the prevalence of hypertension especially of systolic level. The incidence is more in urban than in rural population. Prevalence is slightly more in women (Gupta, 1997). Cardiovascular deaths in India are estimated to be 2.5 million per year and by 2020 it will be the leading cause of death (Enas et al 1996). This provides window to our future as we urbanize and adopt unhealthy life styles.

Angiotensin Converting Enzyme: Its Physiology

In the development of blood pressure Renin Angiotensin Aldosteron System (RAAS) plays a major role (Petrillo et al, 1982). It interacts with Kallikrein-Kinin-Prostaglandin System (KKP) to regulate blood pressure. ACE, as it is well known, plays a pivotal role in both the system and helps in keeping homeostasis in blood pressure. The key components of RAAS include Renin, Angiotensinogen, Angiotensin Converting Enzyme, Angiotensin-I, Angiotensin-II & Aldosterone.

Increased ACE activity has also been linked to the hypertrophy of endothelial cells in vasculature by decreasing apoptosis. It causes the narrowing of lumen of vessels, which results in increased blood pressure. High ACE activity also contributes to oxidative stress.

Figure 1:
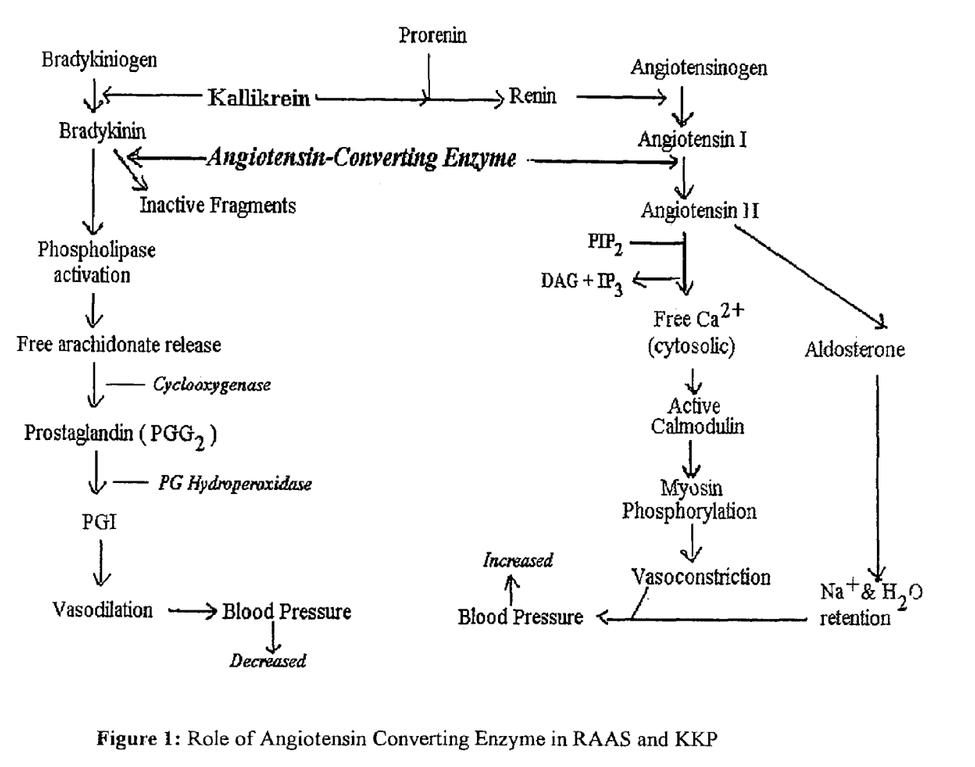
FIG. 1: Role of Angiotensin Converting Enzyme in RAAS and KKP

Kallikrein-Kinin-Prostaglandin is an alternative blood controlling system (FIG. 1) which is influenced by ACE. Kallikrein is a serine protease glycoprotein synsthesised in liver. It acts upon kininogens producing Bradykinin. Bradykinin synthesizes prostaglandins and nitric oxide (NO) that cause the relaxation of smooth muscles leading to a decrease in blood pressure. Angiotensin converting enzyme degrades Bradykinin thus augmenting the blood pressure (Bhoola et al, 1999).

Interaction of Substrate of Angiotensin Converting Enzyme with Its Active Site

Angiotensin converting enzyme (ACE) plays an important role in both above-mentioned systems.

Figure 2:
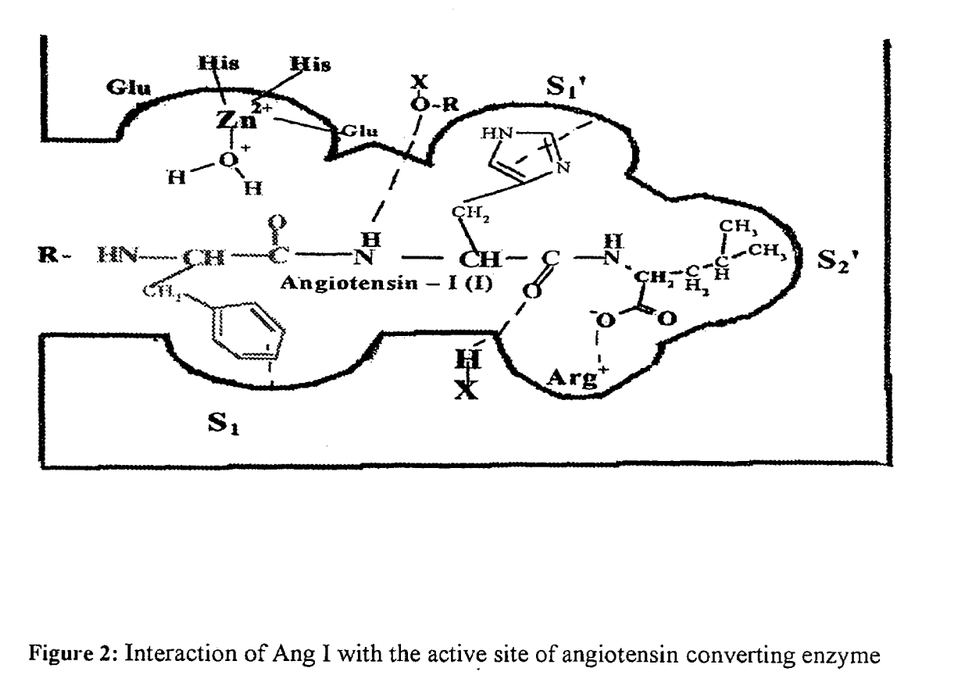
FIG. 2: Interaction of Ang I with the active site of angiotensin converting enzyme

Angiotensin converting enzyme (MW 150-180 KD) is a membrane bound glycoprotein (Ehlers et al, 1989). It has two homologous domains: N-domain and C-domain. It is a Zn metalloprotease (Ehlers et al, 1989) and removes a dipeptide (His-Leu) from C-terminal of Ang-I (FIG. 2) and converting it to Ang-II, which is a potent vaso-constrictor. The active site of ACE has subsites $S_1$, $S_1'$ and $S_2'$. The substrate of ACE, Angiotensin-I, makes hydrophobic interaction with subsites $S_1$, $S_1'$, $S_2'$. While $Zn^{2+}$ & its coordinated-water molecule are present in a fourth subsite. The substrate gets oriented in such a way that it interacts with zinc-coordinated water molecule as shown in the FIG. 2. The glutamate polarizes and activates water molecule to hydrolyze Angiotensin-I into Angiotensin-II and a dipeptide. Increased ACE activity leads to enhanced production of Ang-II and degradation of bradykinin leading to increased BP.

Inhibition of ACE

From above, it can be concluded that ACE by regulating blood pressure is the hub of RAAS and KKP. So it may be deduced that molecules that can reduce ACE activity can be used to counter hypertension because inhibition of ACE leads to two major effects:

(1) Decrease in the conversion of angiotensin I to angiotensin II diminishes the effect of RAAS and thus relaxing the smooth muscles and reduce the production of aldosterone resulting in decrease of blood volume and blood pressure (Giudicelli et al, 1995).
(2) Decrease in bradykinin degradation in KKP system. Bradykinin, when interacts with B2 receptors at endothelial cells, causes the release of endothelium-derived relaxing factors like nitric oxide (NO) and prostaglandin-prostacyclin which cause relaxation of smooth muscles leading to a decrease in BP (Giudicelli et al, 1995).

New Aspects of Inhibition of ACE

Recent reports suggest that advantages of ACE inhibition go beyond its conventional roles because ACEIs (1) Decrease in hypertrophy that may decline the chances of atherosclerosis (Chobanian et al, 1990).
(2) Decrease in oxidative stress by reducing the formation of superoxide anions(Munzel and Keaney, 2001)
(3) Decrease in tissue factor activity that can prevent the development of atherosclerosis (Napoleone et al, 2000).
(4) Decrease in ACE activity can increase the level of Ac-SDKP and it can be used as anti cancer therapy (Azizi et al, 1996).

In view of the above-mentioned roles of ACE inhibitors in various disorders, several groups of researchers are engaged in developing drug targets as angiotensin converting enzyme inhibitors.

Current Status of Hypertension Therapies:

Angiotensin Converting Enzyme Inhibitors (ACEIs)

Several vasodilating agents have been synthesized in treatment of congestive heart failure and hypertension Nitrates like isosorbide mononitrate and glyceryl trinitrates are used to counter hypertension (Winbury and Gabel, 1967) but they have a short duration of action (Cohn, Johnson and Ziesche et at, 1991). A diuretic like thiazide increases the excretion of water and along with it sodium. A decrease in sodium leads to hypovolumia resulting in decreased BP. One of the main shortcoming of diuretics is hypokalemia (Brater, 1998). $Ca^+$ plays an important role in muscle contraction. $Ca^+$ channel blockers inhibit influx of $Ca^+$ and do not let the blood pressure rise (Weiner, 1994). Side effects of headache, dizziness and flushing along with peripheral edema are most prominent with Ca channel blockers (Psaty et al, 1995). β-blockers are also among the font line therapy for hypertension. They block the sympathetic beta-receptors, which prevent sympathetic stimulation of heart rate and cardiac metabolism. Side effects of Beta-blockers are light-headedness, postural hypotension, cold extremities, gastric upset with heartburn, diarrhea and impotence (Quyyumi et al, 1984).

Renin-Angiotensin-Aldosteron System plays the pivotal in development of hypertension. The main acting agent of this system is Ang II, which is a potent vasoconstrictor. There are two main strategies that do not let the Ang II elicit its vasoconstrictive effects. First is AT1 receptor antagonist, which do not let Ang II bind to its AT1 receptors (Goodfriend et al, 1996). Second therapy dealing with RAAS is Angiotensin Converting Enzyme Inhibitors. These inhibitors competitively bind to the active site of ACE and do not let natural substrates (Ang I & Bradkinin) bind to the active site. Captoprils, Enalpril are main ACE inhibitor.

ACEIs are the most important among the drugs controlling hypertension. All the drugs currently available in the market have a more or less similar mode of action. These drugs inhibit the activity of ACE as depicted in the FIG. 1 that leads to decreased formation of Ang II reducing BP.

The main drugs currently available in the market are captopril, enalpril, fosinopril, ramipril and lisinopril.

Captopril is a derivative of proline and D-2-Methyle-3-mercaptopropionic acid whose SH group efficiently interacts with Zn in active site and replaces the water molecule. (Cushman and Ondetti, 1991).

Enalpril has proline and alanine derived moiety whose $COO^-$ group interacts with Zn in active site. It is a prodrug that is converted by esterase activity in liver to more active enalprilate (Patchett et at, 1980).

Fosinopril is a derivative of proline and acetic acid derivative with phosphate group that interacts with Zn. Its absorption is rapid. By esterase activity it is converted to fosinoprilate (Singhvi et al, 1988).

Ramipril is a carboxylated dipeptide inhibitor prodrug. In body it is converted into diacid ramiprilate (Vasment and Bender, 1989).

Limitations of Current ACE Inhibitors (1) Since most of the ACE inhibitors, synthesized so far, are peptide based. Their peptide nature makes them susceptible to proteolytic degradation and the body excretes them. Due to this reason, ACE inhibitors show less bioavailability and therefore repeated and larger doses are needed to have the desired effects (Gavras and Gavras, 1980).
(2) Sometimes ACE inhibitors lead to accumulation of bradykinin in air passages resulting in bronchospasm and dry-cough (Israili and Hall, 1992).
(3) ACE inhibitor therapy is some times associated with angioedema in which watery fluid is collected under skin, mucous membrane or subcutaneous tissue that sometimes erupt to form boils on skin (Israili and Hall, 1992).
(4) The ACE inhibitors, due to presence of different functional groups, cause rashes, ski irritation, neutropenia and taste alteration (DiBianco, 1986).
(5) Most of the ACE inhibitors cause hypotension. The frequency of hypotension is higher in case of diuretic intake (Hodsman et al, 1983).
(6) They also cause a decline in renal function. During ACE inhibition efferent arteriolar resistance decreases and glomerular filtration declines (Hricik et al, 1983).
(7) ACE inhibitors also cause hyperkalemia because aldosterone is inhibited (Warren and O'Connor, 1980).

Peptidomimics: A New Approach

The side effects of these inhibitors have resulted in renewed efforts in modifying the available drugs or developing new drugs with minimum side effects and longer bioavailability. Despite the significant efforts to develop ACE inhibitors devoid of the above said side effects, progress has been disappointed. Moreover currently available ACEIs are peptide-based compounds which are proteolysed by various proteases and excreted by body.

However to the best of our knowledge, no attempt has been made to modify the peptidic nature of these inhibitors in order to inhibit the proteolytic cleavage by various proteases to enhance the longevity as well as their better interaction in the active site. A new emerging concept in the form of peptidomimics seems to be the right answer to this problem (Beelay, 1994).

Peptidomimcs are synthesized by combining peptidic moiety to nonpeptidic moiety. The nonpeptide moieties used include unusual amino acids, some non-toxic, pharmacophoric heterocyclics and diphenyls. These peptidomimics cam be used as ACE inhibitor because they can be resistant to proteolysis and have good interaction with active site.

OBJECTS OF THE INVENTION

The main objective of the present invention is to provide a process for the preparation of novel antihypertensive molecules.

Another objective is to provide a process for the preparation of peptidomimics that can act as ACE inhibitors.

Still another objective is to provide novel antihypertensive ACE inhibiting peptidomimic molecules that have better bioavailability in comparison to available inhibitors.

Another objective is to provide a process to prepare ACE inhibitors that can bind to the active site of ACE by hydrophobic and hydrophilic interaction which can be achieved by proper selection of amino acids Still another objective is to provide a process for the synthesis of ACE inhibitors that can strongly ligate with the Zn present in the active site in such a way that it can not compete with and carry out the hydrolysis of substrate.

Another objective is to provide a process to synthesize ACE inhibitors having nonpeptide moiety or unusual amino acids (pharmacophoric group) that can make a nonpeptide bond resistant against proteolysis.

Another objective is to provide ACE inhibitors that can show selective inhibition of the two active sites i.e. N-domain & C-domain active site of the ACE.

Yet another objective is to provide a process to make a Focussed library of peptidomimics by using Combinatorial Chemistry.

SUMMARY OF THE INVENTION

Accordingly the present invention provides a process for the preparation of novel antihypertensive molecules which comprise
(a) Designing of novel ACE inhibiting antihypertensive molecules designated as peptidomimimcs compound wherein the heterocyclic or unusual amino acid, present at antepenultimate position, is coupled to a dipeptide with amino acids present at ultimate position and penultimate position.
(a) synthesis of dipeptide on solid support by known methods of coupling and deprotection.
(b) coupling of heterocyclic or unusual amino acid to deprotected dipeptide at the N-α terminal of dipeptide.
(c) cleaving of the synthesized peptidomimic compound of step (c) from solid support by known methods followed by purification and characterization by known methods.
(d) in-vitro evaluation of synthesized peptidomimics for ACE inhibiting potency by using synthetic substrate.
(e) in-vivo evaluation of synthesized peptidomimics for its ACE inhibiting efficacy in animal models of hypertension.

In an embodiment to the invention, the synthesis of focussed library of peptidomimics as ACE inhibiting antihypertensive molecule is done by combinatorial chemistry.

In another embodiment of the present invention novel peptide derivatives are synthesized having general formula X—CONH-AA$_1$-CONH-AA$_2$ and X—CH$_2$—NH-AA$_1$-CONH-AA$_2$ wherein CO—NH (amide bond) has been reduced to CH$_2$NH and X is a heterocyclic or unusual amino acid. AA1 and AA2 are amino acids.

In yet another embodiment of the present invention heterocyclic are selected from 3-(2-furyl)-L-alanine, 3-(3-thienyl)-L-alanine, 4-piperazine-1-yl-acetic acid hydrate, 3,3-diphenyl-L-alanine, Azetidine-3-carboxylic acid, Benzimidazolepropionic acid, 1,2,3,4 tetrahydroquinoline-3-carboxylic acid, 2-oxo-4-phenyl-3-oxazolidine-acetic acid, 5-Methoxy-2-methyl-3-indole acetic acid, 5-Mercapto-1-terazole acetic acid.

In still another embodiment of the present invention unusual amino acids for position X may be selected from a group comprising Hydroxytryptophan, L-Abrine, L-β-homoproline, βHomoTrp —OH, Homophenylalanine L-β-homotryptophan, L-2-propargyl glycine, 3,3 Diphenylalanine, L-β-Homohydroxyproline, Cyclohexylalanine.

In an embodiment of the present invention dipeptide, for position AA1-AA2, can be selected from Orn-Pro, Cha-Pro, Ile-Pro, Dap-Pro, Val-Trp, Lys-Pro, Lys-Trp, Orn-Trp, Dap-Trp, Ile-Phe, β-Ala-Pro, Pro-Pro, Cha-Trp.

In still another embodiment of the present invention dipeptide Orn-Pro can be incorporated to various hetrocyclic compound and unusual amino acids to produce L-Abrine-Orn-Pro, 3-(3-thienyl)-L-alanine-Orn-Pro, 3-(2-furyl)-L-alanine-Orn-Pro, 2-Benzimidazoleacetic acid-Orn-Pro, 5-Hydroxytrytophan-Orn-Pro, Homotryptophan-Orn-Pro, Homophenyalanine-Orn-Pro, 1,2,3,4-tetrahydro isoquinoline-3-carboxylic acid-Orn-Pro, Azetidine-3-carboxylic acid-Orn-Pro, Cyclohexylalanine-Orn-Pro, 2-Oxo-4-phenyl-3-oxazolidine acetic acid-Orn-Pro, 4-piperazine acetic acid-Orn-Pro In still another embodiment of the present invention dipeptide Cha-Pro can be coupled to various heterocyclic and unusual amino acids to produce L-Abrine-Cha-Pro, 3-(3-thienyl)-L-alanine-Cha-Pro, 3-(2-furyl)-L-alanine-Cha-Pro, 2-Benzimidazoleacetic acid-Cha-Pro, 5-Hydroxytrytophan-Cha-Pro, Homotryptophan-Cha-Pro, Homophenyalanine-Cha-Pro, 1,2,3,4-tetrahydro isoquinoline-3-carboxylic acid-Cha-Pro, Azetidine-3-carboxylic acid-Cha-Pro, Cyclohexylalanine-Cha-Pro, 2-Oxo-4-phenyl-3-oxazolidine acetic acid-Cha-Pro, 4-piperazine acetic acid-Cha-Pro.

In still another embodiment of the present invention dipeptide Ile-Pro can be coupled to various heterocyclic and unusual amino acids to produce L-Abrine-Ile-Pro, 3-(3-thienyl)-L-alanine-Ile-Pro, 3-(2-furyl)-L-alanine-Ile-Pro, 2-Benzimidazoleacetic acid-Ile-Pro, 5-Hydroxytrytophan-Ile-Pro, Homotryptophan-Ile-Pro Homophenyalanine-Ile-Pro, 1,2,3,4-tetrahydro isoquinoline-3-carboxylic acid-Ile-Pro, Azetidine-3-carboxylic acid-Ile-Pro, Cyclohexylalanine-Ile-Pro, 2-Oxo-4-phenyl-3-oxazolidine acetic acid-Ile-Pro, 4-piperazine acetic acid-Ile-Pro.

In still another embodiment of the present invention dipeptide Dap-Pro can be coupled to various heterocyclic and unusual amino acids to produce L-Abrine-Dap-Pro, 3-(3-thienyl)-L-alanine-Dap-Pro, 3-(2-furyl)-L-alanine-Dap-Pro, 2-Benzimidazoleacetic acid-Dap-Pro, 5-Hydroxytrytophan-Dap-Pro, Homotryptophan-Dap-Pro, Homophenyalanine-Dap-Pro, 1,2,3,4-tetrahydro isoquinoline-3-carboxylic acid-Dap-Pro, Azetidine-3-caboxylic acid-Dap-Pro, Cyclohexylalanine-Dap-Pro, 2-Oxo-4-phenyl-3-oxazolidine acetic acid-Dap-Pro, 4-piperazine acetic acid-Dap-Pro.

In still another embodiment of the present invention dipeptide Val-Trp can be coupled to various heterocyclic and unusual amino acids to produce L-Abrine-Val-Trp, 3-(3-thienyl)-L-alanine-Val-Trp, 3-(2-furyl)-L-alanine-Val-Trp, 2-Benzimidazoleacetic acid-Val-Trp, 5-Hydroxytrytophan-Val-Trp, Homotryptophan-Val-Trp, Homophenyalanine-Val-Trp, 1,2,3,4-tetrahydro isoquinoline-3-carboxylic acid-Val-Trp, Azetidine-3-carboxylic acid-Val-Trp, Cyclohexylalanine-Val-Trp, 2-Oxo-4-phenyl-3-oxazolidine acetic acid-Val-Trp, 4 -piperazine acetic acid-Val-Trp.

In still another embodiment of the present intention dipeptide Lys-Pro can be coupled to various heterocyclic and unusual amino acids to produce L-Abrine-Lys-Pro, 3-(3-thienyl)-L-alanine-Lys-Pro, 3-(2-furyl)-L-alanine-Lys-Pro, 2-Benzimidazoleacetic acid-Lys-Pro, 5-Hydroxytophan-Lys-Pro, Homotryptophan-Lys-Pro, Homophenyalanine-Lys-Pro, 1,2,3,4-tetrahydro isoquinoline-3-carboxylic acid-Lys-Pro, Azetidine-3-carboxylic acid-Lys-Pro, Cyclohexylalanine-Lys-Pro, 2-Oxo-4-phenyl-3-oxazolidine acetic acid-Lys-Pro, 4-piperazine acetic acid-Lys-Pro.

In still another embodiment of the present invention dipeptide Lys-Trp can be coupled to various heterocyclic and unusual amino acids to produce L-Abrine-Lys-Trp, 3-(3-thienyl)-L-alanine-Lys-Trp, 3-(2-furyl)-L-alanine-Lys-Trp, 2-Benzimidazoleacetic acid-Lys-Trp, 5-Hydroxrytophan-Lys-Trp, Homotryptophan-Lys-Trp, Homophenyalanine-Lys-Trp, 1,2,3,4-tetrahydro isoquinoline-3-carboxylic acid-Lys-Trp, Azetidine-3-carboxylic acid-Lys-Trp, Cyclohexylalanine-Lys-Trp, 2-Oxo-4-phenyl-3-oxazolidine acetic acid-Lys-Trp, 4-piperazine acetic acid-Lys-Trp.

In still another embodiment of the present invention dipeptide Orn-Trp can be coupled to various heterocyclic and unusual amino acids to produce L-Abrine-Orn-Trp, 3-(3-thienyl)-L-alanine-Orn-Trp, 3-(2-furyl)-L-alanine-Orn-Trp, 2-Benzimidazoleacetic acid-Orn-Trp, 5-Hydroxytrytophan-Orn-Trp, Homotryptophan-Orn-Trp, Homophenyalanine-Orn-Trp, 1,2,3,4-tetrahydro isoquinoline-3-carboxylic acid-Orn-Trp, Azetidine-3-carboxylic acid-Orn-Trp, Cyclohexylalanine-Orn-Trp, 2-Oxo-4-phenyl-3-oxazolidine acetic acid-Orn-Trp, 4-piperazine acetic acid-Orn-Trp.

In still another embodiment of the present invention dipeptide Dap-Trp can be coupled to various heterocyclic and unusual amino acids to produce L-Abrine-Dap-Trp, 3-(3-thienyl)-L-alanine-Dap-Trp, 3-(2-furyl)-L-alanine-Dap-Trp, 2-Benzimidazoleacetic acid-Dap-Trp, 5-Hydroytrytophan-Dap-Trp, Homotryptophan-Dap-Trp, Homophenyalanine-Dap-Trp, 1,2,3,4-tetrahydro isoquinoline-3-carboxylic acid-Dap-Trp, Azetidine-3-carboxylic acid-Dap-Trp, Cyclohexylalanine-Dap-Trp, 2-Oxo4-phenyl-3-oxazolidine acetic acid-Dap-Trp, 4-piperazine acetic acid-Dap-Trp.

In still another embodiment of the present invention dipeptide Ile-Phe can be coupled to various heterocyclic and unusual amino acids to produce L-Abrine-Ile-Phe, 3-(3-thienyl)-L-alanine-Ile-Phe, 3-(2-furyl)-L-alanine-Ile-Phe, 2-Benzimidazoleacetic acid-Ile-Phe, 5-Hydroxytrytophan-Ile-Phe, Homotryptophan-Ile-Phe, Homophenyalanine-Ile-Phe, 1,2,3,4-tetrahydro isoquinoline-3-carboxylic acid-Ile-Phe, Azetidine-3-carboxylic acid-Ile-Phe, Cyclohexylalanine-Ile-Phe, 2-Oxo-4-phenyl-3-oxazolidine acetic acid-Ile-Phe, 4-piperazine acetic acid-Ile-Phe.

In still another embodiment of the present invention dipeptide β-Ala-Pro can be coupled to various heterocyclic and unusual amino acids to produce L-Abrine-βAla-Pro, 3-(3-thienyl)-L-alanine-βAla-Pro, 3-(2-furyl)-L-alanine-β-Ala-Pro, 2-Benzimidazoleacetic acid-β-Ala-Pro, 5-Hydroxytrytophan-β-Ala-Pro, Homotryptophan-β-Ala-Pro, Homophenyalanine-β-Ala-Pro, 1,2,3,4-tetrahydro isoquinoline3-carboxylic acid-βAla-Pro, Azetidine-3-carboxylic acid-β-Ala-Pro, Cyclohexylalanine-β-Ala-Pro, 2-Oxo4-phenyl-3-oxazolidine acetic acid-β-Ala-Pro, 4-piperazine acetic acid-β-Ala-Pro.

In still another embodiment of the present invention dipeptide Pro-Pro can be coupled to various heterocyclic and unusual amino acids to produce L-Abrine-Pro-Pro, 3-(3-thienyl)-L-alanine-Pro-Pro, 3-(2-furyl)-L-alanine-Pro-Pro, 2-Benzimidazoleacetic acid-Pro-Pro, 5-Hydroxytrytophan-Pro-Pro, Homotryptophan-Pro-Pro, Homophenyalanine-Pro-Pro, 1,2,3,4-tetrahydro isoquinoline-3-carboxylic acid-Pro-Pro, Azetidine-3-carboxylic acid-Pro-Pro, Cyclohexylalanine-Pro-Pro, 2-Oxo4-phenyl-3-oxazolidine acetic acid-Pro-Pro, 4-piperazine acetic acid-Pro-Pro.

In still another embodiment of the present invention dipeptide Cha-Trp can be coupled to various heterocyclic and unusual amino acids to produce L-Abrine-Cha-Trp, 3-(3-thienyl)-L-alanine-Cha-Trp, 3-(2-furyl)-L-alanine-Cha-Trp, 2-Benzimidazoleacetic acid-Cha-Trp, 5-Hydroxytrytophan-Cha-Trp, Homotryptophan-Cha-Trp, Homophenyalanine-Cha-Trp, 1,2,3,4-tetrahydro isoquinoline-3-carboxylic acid-Cha-Trp, Azetidine-3-carboxylic acid-Cha-Trp, Cyclohexylalanine-Cha-Trp, 2-Oxo-4-phenyl-3-oxazolidine acetic acid-Cha-Trp, 4-piperazine acetic acid-Cha-Trp.

In yet another embodiment of present invention all the reaction are carried out at room temperature in Dimethylformamide or Dichloromethane.

In an embodiment of the present invention the solid support used are polystyrene resins linked with suitable agent/handles that may be acid labile like 4-hydroxymethylphenoxyacetic acid or hyper acid labile like 4-hydroxymethyl-3methoxy-phenoxyacetic acid and 2-chlorotrityl2-chloride linker.

In another embodiment of the present invention the anchoring of activated C-terminal of the N-α-protected amino acid on to the solid support is carried out by known methods such as symmetrical anhydrides or reactive ester formation method like 1-hydroxybenzotriazole, benzotriazolyloxy-tridimethylamino-phosphonium-hexaflourophosphate and benzotriazole-1-yl-oxy-trispyrrolidino-phosphoniunm-hexaflourophosphate.

In yet another embodiment of the present invention the deprotection of the N-α-protected amino acid may be affected by known methods of removing flouro-methyl-oxy carbonyl group depending on the compatibility with the linking group on the solid support.

In yet another embodiment the present invention the cleavage may be effected by known methods such as by trofluroacetic acid, acetic acid and trifluroethanol depending upon the linking agent/functional group attached on the solid support and the C terminal functional group desired.

In another embodiment the purification is carried out by gel permeation method using sephadex G/LH-20 followed by characterization using techniques of HPLC, MALDI-Tof and LC-MS.

In still another embodiment in-vitro evaluation of synthesized peptidomimics for their ACE inhibiting potency is done by enzyme assay using synthetic substrate Hippuryl-Histidyl-Leucine (HHL).

In yet another embodiment of the invention the concentration of the new peptidomimic compounds for 50% inhibition of ACE activity ($IC_{50}$) is in the range of 2 μmole to 10 μmole in in-vitro assay using synthetic substrate Hippuryl-Histidyl-Leucine (HHL).

In yet another embodiment of the present invention in-vivo evaluation of synthesized peptidomimics for its ACE inhibiting efficacy is done in animal model of hypertension In still another embodiment the dose of the synthesized ACE inhibiting peptidomimic compound which effectively blocked angiotensin converting enzyme is in the range of 5 to 8 mg/kg of body weight.

Other and further aspects, features, and advantages of the present invention will be apparent from the following description of the preferred embodiments of the invention given for the purpose of disclosure. Alternative embodiments of the invention can be envisaged by those skilled in the art. All such alternative embodiments are intended to lie within the scope of this invention.

DETAILED DESCRIPTION OF THE INVENTION

Synthesis of Peptidomimics

For proper drug targeting there is need to synthesize the library of compounds i.e. Peptidomimics. These peptidomimics are being designed according to Structural Activity Relationship, synthesized by Combinatorial Chemistry and their inhibition is checked by In vitro studies.

(a) Designing of Novel Peptidomimics

Peptidomimic compounds that can act as ACE inhibitor preferably must have following features (FIG. 3):
(1) The peptidomimic compound should have aromatic, aliphatic amino acids like Phe, Trp, Tyr Pro (Cheung et al 1980),
(2) A negatively charged COO⁻ group should be present at C-terminal.
(3) Amino acids like Ile, Leu, Lys and Val are incorporated next to the C-terminal amino acid.
(4) In peptidomimic compound the aromatic moieties of currently existing ACEIs are replaced with suitable heterocyclics or unusual amino acids.

Figure 3:
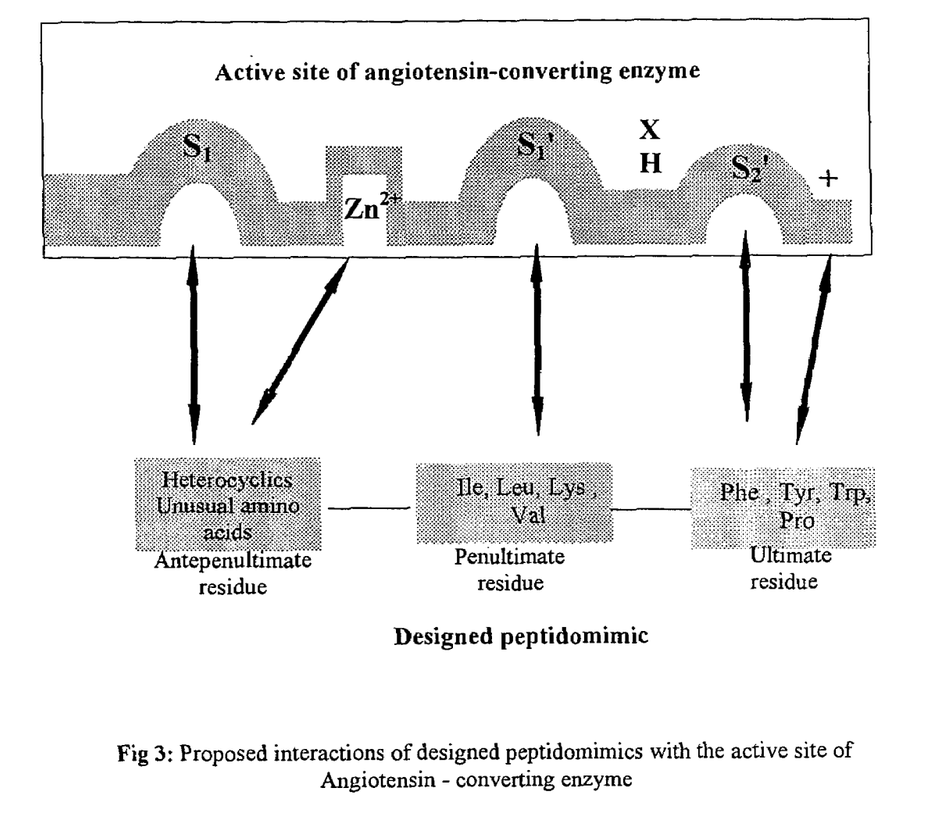
FIG. 3: Proposed interactions of designed peptidomimics with the active site of Angiotensin—converting enzyme

The process of present invention thus results in the synthesis of di and tripeptidomimics consisting of various combinations of aromatic amino acids (Phe, Trp, Tyr and Pro) and aliphatic amino acids (Ile, Leu, Lys and Val). The residues chosen at C-terminal will enhance hydrophobic interactions with subsites S1', S2'. The negatively charged COO⁻ group of these amino acids at C-terminal has hydrophobic interaction with positively charged Arg residue in the enzyme's active site. Hydrophobic side chains of aliphatic amino acids, next to the C-terminal amino acid, establish interaction with ACE hydrophobic subsite S1'. A carbonyl of amide bond of these amino acids forms H-bonds with hydrogen of ACE active site. In new peptidomimics, N-terminal will be substituted with suitable hetrocyclic or unusual amino acids to enhance their bioavailability as well as their interaction with co-ordinated Zn and hydrophobic subsite S1 present in enzyme's active site.

Heterocyclic moieties are the molecules that have certain medicinally functional groups known as 'pharmacophores'. These pharmacophores are supposed to be compatible with human system. These molecules are also expected to produce conformational constraints that help them to interact with active site in a better and effective way.

The work as designed and described above involves synthesis of large number of peptidomimics. This can be best achieved by the combinatorial chemistry, which will be used in the present proposed work.

(b) Synthesis of Peptidomimics: Combinatorial Chemistry

This concept takes its origin with the aim of synthesizing 96 diverse peptides simultaneously (Furk et al, 1991). In this method, in each reaction vessel, peptides with different sequences are synthesized preferably by solid phase peptide synthesis. This technique is of two types:

(1) Multiple Synthesis of Mixture of Peptides

This method involves the synthesis of mixture of large number of peptides called as compound libraries of peptides. In this method, in each reaction vessel peptides with different sequences are simultaneously synthesized. This method, also called pool and split method, involves:
(a) Dividing or splitting of resin into different parts.
(b) Coupling of resin with amino acids.
(c) Mixing of coupled parts of resin and adding new amino acids to generate mixture of peptides.

(2) Multiple Synthesis of Individual Peptides

Multiple synthesis of individual peptides involves synthesis of large number of individual peptides (Beck-sickinger and Jung, 1996) One peptide sequence is synthesized in each reaction vessel. There is no splitting and mixing of reaction products like in previous case. This method requires coupling, washing and deprotection repeatedly.

(c) Evaluation of Inhibition of Peptidomimics (1) In Vitro Study of Peptidomimic Inhibitors The library of peptidomimic compound was evaluated for their ACE inhibition potencies by determining the ACE activity by in-vitro enzyme assay using spectrophotometric method (Cheung et al, 1980). In this assay ACE acts upon synthetic substrate Hip-His-Leu. The following assay components in a final volume of 0.25 ml are incubated for 20 minutes at 37° C.: 100 mM potassium phosphate buffer, pH 8.3, 5 mM Hip-His-Leu, 300 mM NaCl and angiotensin converting enzyme (12 miliunits/ml of assay volume). The rate of hydrolysis of Hip-His-Leu is determined by measuring the absorbance of hippuric acid after extracting into ethyl acetate, evaporation of solvent at 120°C. and redissolution into water. Extracted hippuric acid is then measured by reading absorbance at 228 nm.

(2) In Vivo Study of Peptidomimics as ACE Inhibitors

Evaluation of ACE inhibition of synthesized peptidomimics is done in hypertensive rats. Wistar rats (female, 225-250 gm) were taken and hypertension was induced in these rats by administering the injection of Methylprednisolone per week for two weeks (Elijovich and Krakoff, 1980). After two weeks when rats become hypertensive, the efficacy of synthesized ACE inhibitors is checked in in-vivo conditions by intra venous administration in pharmacologically accepted medium in doses ranging from 5 mg/kg of body weigh to 10 mg/kg of body weight.

The following examples are given for the present invention and should be construed to limit the scope of the present invention.

EXAMPLE 1

Designing of ACE Inhibitors (i) Unusual amino acids are coupled with dipeptide. For example for designing of L-Abrine-Ornithine-Proline, Proline was taken at ultimate position, Ornithine was put at penultimate position and unusual amino acid L-Abrine, present at antepenultimate position, was linked to dipeptide Ornithine-Proline.

Antepenultimate residue — Penultimate residue — Ultimate residue (ii) Heterocyclic compounds are coupled with dipeptide. For example for designing of 3-(3-thienyl)-L-alanine-Ornithine-Proline, Proline was taken at ultimate position, Ornithine was put at penultimate position and heterocyclic compound 3-(3-thienyl)-L-alanine, present at antepenultimate position, was linked to dipeptide Ornithine-Proline.

Antepenultimate residue | Penultimate residue | Ultimate residue

EXAMPLE 2

Synthesis of ACE Inhibitor L-Abrine-Ornithine-Proline (a) 2-Chlorotrityl chloride resin (substitution 1.5 mM/gm) is taken as solid support and swelled in dichlorometane (DCM)
(b) C-terminal of N-α-protected Fmoc-Pro-OH at is coupled by reactive ester formation method of 1-Hydroxybenzotriazole and Diisopropylcarbodiimide (DIPCDI) to the solid support of 2-Chlorotrityl chloride resin.
(c) Deprotection of N-α-terminal protecting Fmoc group of the anchored imino acid Proline by 20% piperidine in dimethyl formamide (DMF).
(d) C-terminal of N-α Fmoc protected Ornithine is activated and coupled by reactive ester formation method of 1-Hydroxybenzotriazole and Diisopropylcarbodiimide (DIPCDI) on to the deprotected α-imino group of the anchored imino acid Proline.
(e) Deprotection of N-α-terminal protecting Fmoc group of Ornithine linked to anchored imino acid Proline by 20% piperidine in dimethyl formamide (DMF).
(f) Unusual amino acid Fmoc-L-Abrine (N-methyltryptophan) is coupled to deprotected N-α-terminal amino acid Ornithine by reactive ester formation method of 1-Hydroxybenzotriazole and Diisopropylcarbodiimide (DIPCDI).
(g) Deprotection of N-α-terminal protecting Fmoc group of L-Abrine linked to dipeptide Ornithine-Proline by 20% piperidine in dimethyl formamide (DMF).
(h) Cleave the peptidomimic L-Abrine-Ornithine-Proline from the solid support by known methods depending upon the side chain protecting groups of amino acids.
  (i) For amino acids with out Boc and Trt group, acetic acid:trifluoroacetic acid:dichlorometane are taken in ratio of 1:1:8. 10 to 20μ litre of ethyldiamine tetra acetate (ETA) and a pinch of phenol are added in to the cleavage mixture. Reaction is carried out for 30 minutes.
  (ii) For Boc containing amino acids trifluoroacetic acid:dichlorometane are taken in ratio of 1:1 (v/v). 10 to 20μ litre of ethyldiamine tetra acetate (EDTA) and a pinch of phenol are added in to the cleavage mixture. Reaction is carried out for 30 minutes.
(j) Cleaved product is purified in LH-20 column using methanol as mobile phase
(k) Purified product is lyophilized.
(l) Product is characterized by HPLC and LC-MS.

EXAMPLE 3

Synthesis of ACE Inhibitor 3-(3-thienyl)-L-alanine-Ornithine-Proline (a) 2-Chlorotrityl chloride resin (substitution 1.5 mM/gm) is taken as solid support and swelled in dichlorometane (DCM)
(b) C-terminal of N-α-protected Fmoc-Pro-OH at is coupled by reactive ester formation method of 1-Hydroxybenzotriazole and Diisopropylcarbodiimide (DIPCDI) to the solid support of 2-Chlorotrityl-chloride resin.
(c) Deprotection of N-α-terminal protecting Fmoc group of the anchored imino acid Proline by 20% piperidine in dimethyl formamide (DMF).
(d) C-terminal of N-α Fmoc protected Ornithine is activated and coupled by reactive ester formation method of 1-Hydroxybenzotriazole and Diisopropylcarbodiimide (DIPCDI) on to the deprotected α-imino group of the anchored imino acid Proline.
(e) Deprotection of N-α-terminal protecting Fmoc group of Ornithine linked to anchored imino acid Proline by 20% piperidine in dimethyl formamide (DMF).
(f) Heterocyclic 3-(3-thienyl)-L-alanine is coupled to deprotected N-α-terminal amino acid Ornithine by reactive ester formation method of 1-Hydroxybenzotriazole and Diisopropylcarbodiimide (DIPCDI).
(g) Deprotection of N-α-terminal protecting Fmoc group of 3-(3-thienyl)-L-alanine linked to dipeptide Ornithine-Proline by 20% piperidine in dimethyl formamide (DMF).
(h) Cleaving the peptidomimic 3-(3-thienyl)-L-alanine-Ornithine-Proline from the solid support by known methods depending upon the side chain protecting groups of amino acids.
  (i) For amino acids with out Boc and Trt soup, acetic acid:trifluoroacetic acid:dichlorometane are taken in ratio of 1:1:8. 10 to 20μ litre of ethyldiamine tetra acetate (EDTA) and a pinch of phenol are added in to the cleavage mixture. Reaction is carried out for 30 minutes.
  (ii) For Boc containing amino acids trifluoroacetic acid:dichlorometane are taken in ratio of 1:1 (v/v). 10 to 20μ litre of ethyldiamine tetra acetate (EDTA) and a pinch of phenol are added in to the cleavage mixture. Reaction is carried out for 30 minutes.
(i) Cleaved product is purified in LH-20 column using methanol as mobile phase
(j) Purified product is lyophilized.
(k) Product is characterized by HPLC and LC-MS.

EXAMPLE 4

Synthesis of ACE Inhibitor 2-Oxo-4-phenyl-3-oxazolidine Acetic Acid-Lys-Trp (a) 2-Chlorotrityl chloride resin (substitution 1.5 mM/gm) is taken as solid support and swelled in dichlorometane (DCM)
(b) C-terminal of N-α-protected Fmoc-Trp-OH at is coupled by reactive ester formation method of 1-Hydroxybenzotriazole and Diisopropylcarbodiimide (DIPCDI) to the solid support of 2-Chlorotrityl-chloride resin.
(c) Deprotection of N-α-terminal protecting Fmoc group of the anchored amino acid Tryptophan by 20% piperidine in dimethyl formamide (DMF).
(d) C-terminal of N-α Fmoc protected Lysine is activated and coupled by reactive ester formation method of 1-Hydroxybenzotriazole and Diisopropylcarbodiimide (DIPCDI) on to the deprotected α-imino group of the anchored amino acid Tryptophan.
(e) Deprotection of N-α-terminal protecting Fmoc group of Lysine linked to anchored imino acid Proline by 20% piperidine in dimethyl formamide (DMW).
(f) Heterocyclic 2-Oxo4-phenyl-3-oxazolidine acetic acid is coupled to deprotected N-α-terminal amino acid Lysine by reactive ester formation method of 1-Hydroxybenzotriazole and Diisopropylcarbodiimide (DIPCDI).
(g) Deprotection of N-α-terminal protecting Fmoc group of 2-Oxo-4-phenyl-3-oxazolidine acetic acid linked to dipeptide Lysine-Trytophan by 20% piperidine in dimethyl formamide (DMF).
(h) Cleaving the peptidomimic 2-Oxo-4-phenyl-3-oxazolidine acetic acid-Lys-Trp from the solid support by known methods depending upon the side chain protecting groups of amino acids.
  (i) For amino acids with out Boc and Trt group, acetic acid:trifluoroacetic acid:dichlorometane are taken in ratio of 1:1:8. 10 to 20μ litre of ethyldiamine tetra acetate (EDTA) and a pinch of phenol are added in to the cleavage mixture. Reaction is carried out for 30 minutes.
  (ii) For Boc containing amino acids trifluoroacetic acid:dichlorometane are taken in ratio of 1:1 (v/v). 10 to 20μ litre of ethyldiamine tetra acetate (EDTA) and a pinch of phenol are added in to the cleavage mixture. Reaction is carried out for 30 minutes.
(i) Cleaved product is purified in LH-20 column using methanol as mobile phase
(j) Purified product is lyophilized.
(k) Product is characterized by HPLC and LC-MS.

EXAMPLE 5

Synthesis of ACE Inhibitor
5-Hydroxytryptophan-Ornithine-Tryptophan (a) 2-Chlorotrityl chloride resin (substitution 1.5 mM/gm) is taken as solid support and swelled in dichlorometane (DCM)
(b) C-terminal of N-α-protected Fmoc-Trp-OH at is coupled by reactive ester formation method of 1-Hydroxybenzotriazole and Diisopropylcarbodiimide (DIPCDI) to the solid support of 2-Chlorotrityl-chloride resin.
(c) Deprotection of N-α-terminal protecting Fmoc group of the anchored amino acid Tryptophan by 20% piperidine in dimethyl formamide (DMF).
(d) C-terminal of N-α Fmoc protected Ornithine is activated and coupled by reactive ester formation method of 1-Hydroxybenzotriazole and Diisopropylcarbodiimide (DIPCDI) on to the deprotected α-amino group of the anchored amino acid Tryptophan.
(e) Deprotection of N-α-terminal protecting Fmoc group of Ornithine linked to anchored amino acid Tryptophan by 20% piperidine in dimethyl formamide (DMF).
(f) Unusual amino acid Fmoc 5-Hydroxytryptophan is coupled to deprotected N-α-terminal amino acid Ornithine by reactive ester formation method of 1-Hydroxybenzotriazole and Diisopropylcarbodiimide (DIPCDI).
(g) Deprotection of N-α-terminal protecting Fmoc group of 5-Hydroxytryptophan linked to dipeptide Ornithine-Tryptophan by 20% piperidine in dimethyl formamide (DMF).
(h) Cleaving the peptidomimic 5-Hydroxytryptophan-Ornithine-Tryptophan from the solid support by known methods depending upon the side chain protecting groups of amino acids.
  (i) For amino acids with out Boc and Trt group, acetic acid:trifluoroacetic acid:dichlorometane are taken in ratio of 1:1:8. 10 to 20μ litre of ethyldiamine tetra acetate (EDTA) and a pinch of phenol are added in to the cleavage mixture. Reaction is carried out for 30 minutes.
  (ii) For Boc containing amino acids trifluoroacetic acid:dichlorometane are taken in ratio of 1:1 (v/v). 10 to 20μ litre of ethyldiamine tetra acetate (EDTA) and a pinch of phenol are added in to the cleavage mixture. Reaction is carried out for 30 minutes.
(i) Cleaved product is purified in LH-20 column using methanol as mobile phase
(j) Purified product is lyophilized.
(k) Product is characterized by HPLC and LC-MS.

EXAMPLE 6

Synthesis of ACE Inhibitor Benzimidazoleacetic
Acid-Cyclohexylalanine-Trptophan (a) 2-Chlorotrityl chloride resin (substitution 1.5 mM/gm) is taken as solid support and swelled in dichlorometane (DCM)
(b) C-terminal of N-αprotected Fmoc-Trp-OH at is coupled by reactive ester formation method of 1-Hydroxybenzotriazole and Diisopropylcarbodiimide (DIPCDI) to the solid support of 2-Chlorotrityl-chloride resin.
(c) Deprotection of N-α-terminal protecting Fmoc group of the anchored amino acid Tryptophan by 20% piperidine in dimethyl formamide (DMF).
(d) C-terminal of N-α Fmoc protected Cyclohexylalanine is activated and coupled by reactive ester formation method of 1-Hydroxybenzotriazole and Diisopropylcarbodiimide (DIPCDI) on to the deprotected α-amino group of the anchored amino acid Tryptophan.
(e) Deprotection of N-α-terminal protecting Fmoc group of Cyclohexylalanine linked to anchored amino acid Tryptophan by 20% piperidine in dimethyl formamide (DMF).
(f) Heterocyclic Benzimidazoleacetic acid is coupled to deprotected N-αterminal amino acid Cyclohexylalanine by reactive ester formation method of 1-Hydroxybenzotriazole and Diisopropylcarbodiimide (DIPCDI).
(g) Cleaving the peptidomimic Benzimidazoleacetic acid-Cyclohexylalanine-Tryptophan from the solid support by known methods depending upon the side chain protecting groups of amino acids.
  (i) For amino acids with out Boc and Trt group, acetic acid:trifluoroacetic acid:dichlorometane are taken in ratio of 1:1:8. 10 to 20μ litre of ethyldiamine tetra acetate (EDTA) and a pinch of phenol are added in to the cleavage mixture. Reaction is carried out for 30 minutes.
  (ii) For Boc containing amino acids trifluoroacetic acid:dichlorometane are taken in ratio of 1:1 (v/v). 10 to 20μ litre of ethyldiamine tetra acetate (EDTA) and a pinch of phenol are added in to the cleavage mixture. Reaction is carried out for 30 minutes.
(h) Cleaved product is purified in LH-20 column using methanol as mobile phase
(i) Purified product is lyophilized.
(j) Product is characterized by HPLC and LC-MS.

EXAMPLE 7

Synthesis of ACE Inhibitor
L-Abrine-Isoleucine-Phenylalanine (a) 2-Chlorotrityl chloride resin (substitution 1.5 mM/gm) is taken as solid support and swelled in dichlorometane (DCM)
(b) C-terminal of N-α-protected Fmoc-Phe-OH at is coupled by reactive ester formation method of 1-Hydroxybenzotriazole and Diisopropylcarbodiimide (DIPCDI) to the solid support of 2-Chlorotrityl-chloride resin.
(c) Deprotection of N-α-terminal protecting Fmoc group of the anchored amino acid Phenylalanine by 20% piperidine in dimethyl formamide (DMF).
(d) C-terminal of N-α Fmoc protected Isoleucine is activated and coupled by reactive ester formation method of 1-Hydroxybenzotriazole and Diisopropylcarbodiimide (DIPCDI) on to the deprotected α-amino group of the anchored amino acid Phenylalanine.
(e) Deprotection of N-α-terminal protecting Fmoc group of Isoleucine linked to anchored amino acid Phenylalanine by 20% piperidine in dimethyl formamide (DMF).
(f) Unusual amino acid Fmoc-L-Abrine (N-methyltryptophan) is coupled to deprotected N-α-terminal amino acid Isoleucine by reactive ester formation method of 1-Hydroxybenzotriazole and Diisopropylcarbodiimide (DIPCDI).
(g) Deprotection of N-α-terminal protecting Fmoc group of L-Abrine linked to dipeptide Isoleucine-Phenylalanine by 20% piperidine in dimethyl formamide (DMF).
(h) Cleaving the peptidomimic L-Abrine-Isoleucine-Phenylalanine from the solid support by known methods depending upon the side chain protecting groups of amino acids.
  (i) For amino acids with out Boc and Trt group, acetic acid:trifluoroacetic acid:dichlorometane are taken in ratio of 1:1:8. 10 to 20µ litre of ethyldiamine tetra acetate (EDTA) and a pinch of phenol are added in to the cleavage mixture. Reaction is carried out for 30 minutes.
  (ii) For Boc containing amino acids trifluoroacetic acid:dichlorometane are taken in ratio of 1:1 (v/v). 10 to 20µ litre of ethyldiamine tetra acetate (EDTA) and a pinch of phenol are added in to the cleavage mixture. Reaction is carried out for 30 minutes.
(i) Cleaved product is purified in LH-20 column using methanol as mobile phase
(j) Purified product is lyophilized.
(k) Product is characterized by HPLC and LC-MS.

EXAMPLE 8

Synthesis of ACE Inhibitor 1,2,3,4-tetrahydroisoquinoline-3-carboxylic Acid-Pro-Pro (a) 2-Chlorotrityl chloride resin (substitution 1.5 mM/gm) is taken as solid support and swelled in dichlorometane (DCM)
(b) C-terminal of N-α-protected Fmoc-Pro-OH at is coupled by reactive ester formation method of 1-Hydroxybenzotriazole and Diisopropylcarbodiimide (DIPCDI) to the solid support of 2-Chlorotrityl-chloride resin.
(c) Deprotection of N-α-terminal protecting Fmoc group of the anchored imino acid Proline by 20% piperidine in dimethyl formamide (DMF).
(d) C-terminal of N-α Fmoc protected Pro is activated and coupled by reactive ester formation method of 1-Hydroxybenzotriazole and Diisopropylcarbodiimide (DIPCDI) on to the deprotected α-imino group of the anchored amino acid Pro.
(e) Deprotection of N-α-terminal protecting Fmoc group of Proline linked to anchored imino acid Proline by 20% piperidine in dimethyl formamide (DMF).
(f) Unusual ammo acid 1,2,3,4-tetrahydroisoquinoline-3-carboxylic acid is coupled to deprotected N-α-terminal I imino acid Proline by reactive ester formation method of 1-Hydroxybenzotriazole and Diisopropylcarbodiimide (DIPCDI).
(g) Deprotection of N-α-terminal protecting Fmoc group of 1,2,3,4-tetrahydroisoquinoline-3-carboxylic acid linked to dipeptide Pro-Pro by 20% piperidine in dimethyl formamide (DMF).
(h) Cleaving the peptidomimic 1,2,3,4-tetrahydroisoquinoline-3-carboxylic acid-Pro-Pro from the solid support by known methods depending upon the side chain protecting groups of amino acids.
  (i) For amino acids with out Boc and Trt group, acetic acid:trifluoroacetic acid:dichlorometane are taken in ratio of 1:1:8. 10 to 20µ litre of ethyldiamine tetra acetate (EDTA) and a pinch of phenol are added in to the cleavage mixture. Reaction is carried out for 30 minutes.
  (ii) For Boc containing amino acids trifluoroacetic acid:dichlorometane are taken in ratio of 1:1 (v/v). 10 to 20µ litre of ethyldiamine tetra acetate (EDTA) and a pinch of phenol are added in to the cleavage mixture. Reaction is carried out for 30 minutes.
(i) Cleaved product is purified in LH-20 column using methanol as mobile phase
(j) Purified product is lyophilized.
(k) Product is characterized by HPLC and LC-MS.

EXAMPLE 9

Synthesis of ACE Inhibitor 3-(2furyl)-L-Alanine-β-Alanine-Pro (a) 2-Chlorotrityl chloride resin (substitution 1.5 mM/gm) is taken as solid support and swelled in dichlorometane (DCM)
(b) C-terminal of N-α-protected Fmoc-Pro-OH at is coupled by reactive ester formation method of 1-Hydroxybenzotriazole and Diisopropylcarbodiimide (DIPCDI) to the solid support of 2-Chlorotrityl-chloride resin.
(c) Deprotection of N-α-terminal protecting Fmoc group of the anchored imino acid Proline by 20% piperidine in dimethyl formamide (DMW).
(d) C-terminal of N-α Fmoc protected β-Alanine is activated and coupled by reactive ester formation method of 1-Hydroxybenzotriazole and Diisopropylcarbodiimide (DIPCDI) on to the deprotected α-imino group of the anchored amino acid Pro.
(e) Deprotection of N-α-terminal protecting Fmoc group of β-Alanine linked to anchored imino acid Proline by 20% piperidine in dimethyl formamide (DMF).
(f) Heterocyclic 3-(2-furyl)-L-Alanine is coupled to deprotected N-α-terminal β-Alanine by reactive ester formation method of 1-Hydroxybenzotriazole and Diisopropylcarbodiimide (DIPCDI).
(g) Deprotection of N-α-terminal protecting Fmoc group of 3-(2-furyl)-L-Alanine linked to dipeptide β-Alanine-Pro by 20% piperidine in dimethyl formamide (DMF).
(h) Cleaving the peptidomimic 3-(2-furyl)-L-Alanine-β-Alanine-Pro from the solid support by known methods depending upon the side chain protecting groups of amino acids.
  (i) For amino acids with out Boc and Trt group, acetic acid:trifluoroacetic acid:dichlorometane are taken in ratio of 1:1:8. 10 to 20µ litre of ethyldiamine tetra acetate (EDTA) and a pinch of phenol are added in to the cleavage mixture. Reaction is carried out for 30 minutes.

(ii) For Boc containing amino acids trifluoroacetic acid: dichlorometane are taken in ratio of 1:1 (v/v). 10 to 20μ litre of ethyldiamine tetra acetate (EDTA) and a pinch of phenol are added in to the cleavage mixture. Reaction is carried out for 30 minutes.
(i) Cleaved product is purified in LH-20 column using methanol as mobile phase
(j) Purified product is lyophilized.
(k) Product is characterized by HPLC and LC-MS.

EXAMPLE 10

On the basis of the results of example 2-9 and according to same procedure as in example 2-9 all the peptidomimics, mentioned above, having general formula X—CX1—NH-AA$_1$-CONH-AA$_2$ wherein X is a heterocyclic or unusual amino acid, X1 is O or H$_2$ and AA1 and AA2 are amino acids, are synthesized by using combinatorial chemistry.

EXAMPLE 11

In-vitro Evaluation of ACE Inhibition of Synthesized Peptidomimics

Figure 4:
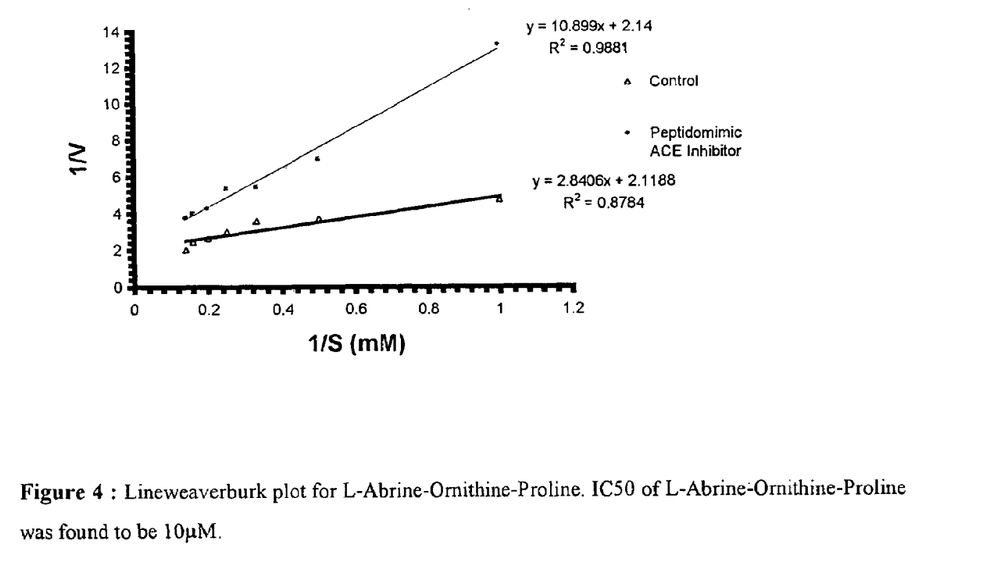
FIG. 4: Lineweaverburk plot for L-Abrine-Ornithine-Proline. IC50 of L-Abrine-Ornithine-Proline was found to be 10 μM.

The peptidomimic compound L-Abrine-Ornithine-Proline was evaluated for its ACE inhibition potency by determining the ACE activity assay using spectrophotometric method. In this assay ACE acts upon synthetic substrate Hip-His-Leu. The following assay components in a final volume of 0.25 ml are incubated for 20 minutes at 37° C.: 100 mM potassium phosphate buffer, pH 8.3, 5 mM Hip-His-Leu, 300 mM NaCl and angiotensin converting enzyme (12 miliunits/ml of assay volume). The rate of hydrolysis of Hip-His-Leu is determined by measuring the absorbance of hippuric acid after extracting into ethyl acetate, evaporation of solvent at 120° C. and redissolution into water. Extracted hippuric acid is then measured by reading absorbance at 228 nm. L-Abrine-Ornithine-Proline and 3-(3-thienyl)-L-alanine-Ornithine-Proline were evaluated for their ACE inhibition efficacy by this assay. 3-(3-thienyl)-L-alanine-Ornithine-Proline showed its IC$_{50}$ to be 2 μ mole. The IC$_{50}$ of L-Abrine-Ornithine-Proline was found to be 10 μ mole. Inhibition kinetics of L-Abrine-Ornithine-Proline is illustrated in FIG. 4. The control experiment contained no peptidomimic ACE inhibitor.

EXAMPLE 12

Development of Animal Model for Hypertension

Female wistar rats with an initial body weight of 225-250 gm were used in this experiment. Three groups of animals were made: Group I (n=3) of control animals; Group II (n=3) of animals for reference inhibitor captopril and Group III (n=5) of animal for synthesized ACE inhibitors Measurement of body weight and tail systolic blood pressure were made in unanesthetsized animals.

Figure 5:
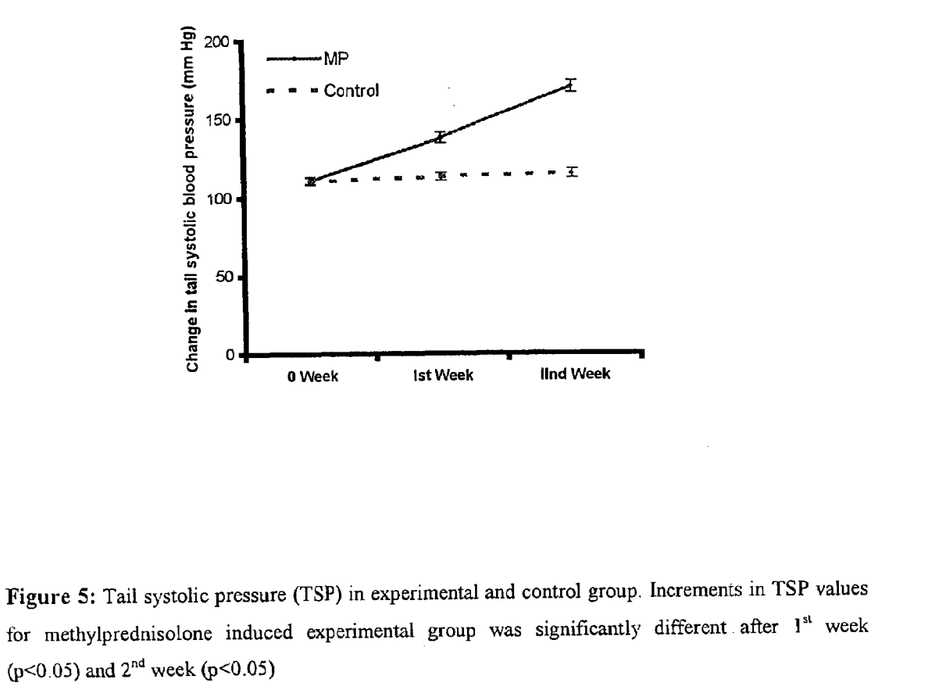
FIG. 5: Tail systolic pressure (TSP) in experimental and control group. Increments in TSP values for methylprednisolone induced experimental group was significantly different after $1^{st}$ week ($p<0.05$) and $2^{nd}$ week ($p<0.05$).

A long acting suspension of 20 mg/kg methylprednisolone (Depo-Medrol, Pharmacia) was administered subcutaneously per week for two weeks in animals of group II and III. Group I of control animals received only vehicle polyethylene glycol (PEG). All animals had free access to tap water, were placed on regular rat chow and had their tail systolic pressure measured every week for two weeks. After two weeks of treatment, all the animal a became significantly hypertensive (FIG. 5).

EXAMPLE 13

In-vivo Administration of Synthesized Peptidomimics as ACE Inhibitor (a) Surgical Procedure The rats were anaesthetized by intraperitoneal administration of urethane (1 gm/kg). The trachea was cannulated with polyethylene tube. Polyethylene cannulas were also placed into the rat femoral artery and vein. The arterial catheter was used for recording of blood pressure and the venous catheter was used for the administration of drugs/peptides. After surgery, animals were allowed 30 min for stabilization before starting the experiment.

(b) Physiological Measurement

Arterial blood pressure was measured with a pressure transducer (WPI-model BPLR) with a strain gauge/bridge amplifier (WPI-model TBM4) connected to four channel digital oscillograph Tektronix (Model TDS 420A). Permanent records were obtained by storing and copying on a floppy disk from the oscillograph. From the arterial blood pressure waveform, mean arterial pressure and diastolic blood pressure were measured.

(c) Drug Administration

Varying amounts of L-Abrine-Ornithine-Proline (5 mg/kg, 8 mg/kg and 10 mg/kg) were dissolved in normal saline. Peptidomimics was injected i.v. in constant volume of 0.2 ml over a period of 10 seconds and the venous catheter was flushed with an additional 0.3 ml of saline. Readings of mean arterial pressure (MAP) were made after each 10 minutes till blood pressure returned to base line.

EXAMPLE 14

Hypotensive Effect of Synthesized Peptidomimics as ACE Inhibitor

Figure 6:
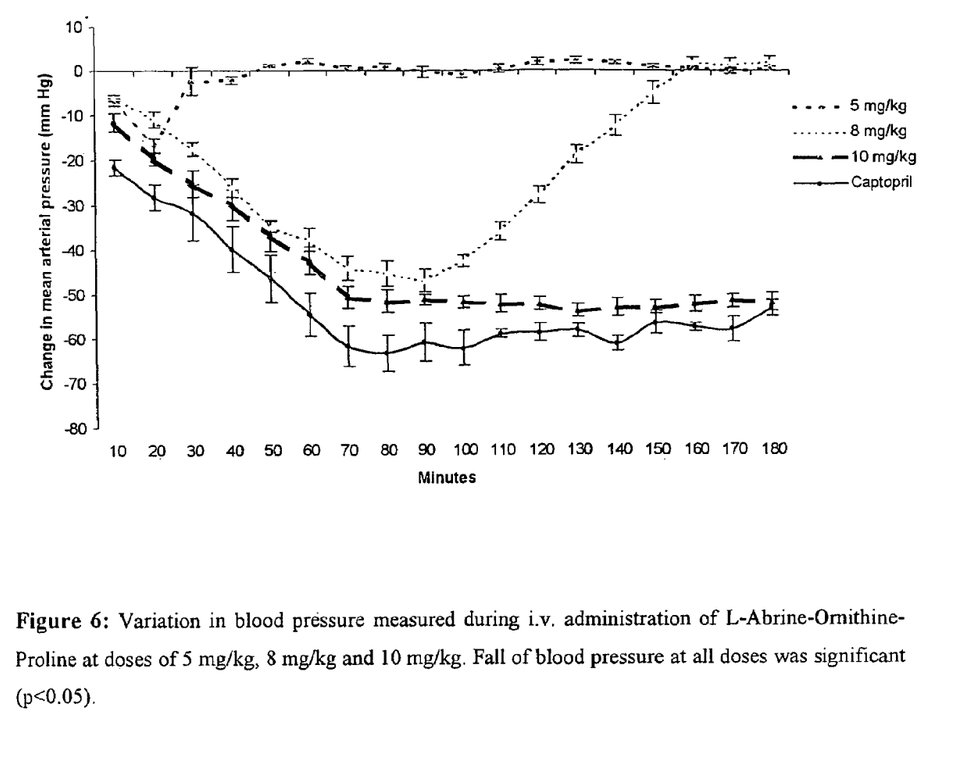
FIG. 6: Variation in blood pressure measured during i.v. administration of L-Abrine-Ornithine-Proline at doses of 5 mg/kg, 8 mg/kg and 10 mg/kg. Fall of blood pressure at all doses was significant ($p<0.05$).

At 5mg/kg L-Abrine-Ornithine-Proline showed its hypotensive effect which caused a fall of around 15 mm Hg (FIG. 6). Hypotensive effect started after almost five minutes and blood pressure returned to baseline within 30 minutes. A dose of 8 mg/kg of L-Abrine-Ornithine-Proline began to show its hypotensive effect five minute after its administration. At this dose, blood pressure declined upto 46 mm Hg. It nearly took 160 minutes for blood pressure to return to baseline. The highest dose used was 10 mg/kg. It showed strong hypotensive effect. The onset of hypotensive effect was again after five minutes of administration. A fall in blood pressure of almost 50 mmHg was reached within 70 minutes and blood pressure did not return to baseline even after 180 minutes Reference inhibitor captopril was used at dose of 1 mg/kg. This dose of captopril caused fall of 60 mm Hg and was quite effective in blocking angiotensin-converting enzyme even after 180 minutes and blood pressure returned to baseline after 240 minutes (not shown).

Advantages of the Present Invention

The present invention adds following advantages to the ACE inhibiting antihypertensive molecule as (a) It provides a process for the preparation of novel antihypertensive molecule.
(b) It provides a process for the synthesis of peptidomimics that can act as ACE inhibitors.

(c) It provides a process to synthesize ACE inhibitors that have better bioavailability in comparison to available inhibitors.
(d) It provides a process to synthesize ACE inhibitors that can strongly ligate the Zn present in the active site in such a way that it can not compete with and carry out the hydrolysis of substrate.
(e) It provides a process to make ACE inhibitors having nonpeptide moiety or unusual amino acids (pharmacophoric group) that can make a nonpeptide bond resistant against proteolysis.
(f) It provides a process to make ACE inhibitors that can show selective inhibition of the two active sites i.e. N-domain & C-domain active site of the ACE.
(g) It provides a process to make Focussed Library of peptidomimics by using Combinatorial Chemistry.

REFERENCES

1. Gupta R, Meta-analysis of hypertension in India, *Indian Heart J,* 1997; 49:43-48.
2. Enas E. A, Dhawan J, Petkar S, "CAD in Asian Indians: Lessons learnt and role of lipoprotein a", *Indian Heart J,* 1996:49:25.
3. Petrillo E. W, Ondetii M. A, Angiotensin converting enzyme inhbitors: Medicinal chemistry and biological action, *Med. Res. Rev,* 2:1-41; 1982.
4. Bhoola K. D, Figueroa C. D, Worthy K, Bioregulation of kinins: Kalikreins, Kininogen & Kininases, *Pharmacol. Rev.,* 44:180,1999.
5. Ehlers M. R. W, Riordan J. F, Angiotensin converting enzyme: New concepts concerning its biological role, *Biochemistry,* 28:5311-5318, 1989.
6. Giudicelli J F, Berdeaux A, Richer C, Pussard E, Demolis P, Basic cardiovascular pharmacology of ACE inhibitors. In: Schachter M, ed. ACE inhibitors: Current use and future prospects: Martin Dunitz Ltd. Londen, 43-62; 1995.
7. Chobanian A V, Haudenschild C C, Nickerson C, Drago R Anti-atherogenic effect of captopril in the Watanabe heritable hyperlipidemic rabbit. *Hypertension,* 1990; 15: 327-331.
8. Munzel T, Keaney J F Jr. Are ACE inhibitors a "magic bullet" against oxidative stress? *Circulation.* 2001 Sep. 25; 104(13):1571-4.
9. Napoleone E, Santo A D, Camera M, Tremoli E, Lorenzet R. Angiotensin converting enzyme inhibitors downregulate tissue factor synthesis in monocytes. *Circulation Research,* 2000 Feb. 4; 86(2):139-43.
10. Azizi M, Rousseau A, Ezan E, Guyene T T, Michelet S, Grognet J M, Lenfant M, Corvol P, Menard J. Acute angiotensin-converting enzyme inhibition increases the plasma level of the natural stem cell regulator N-acetyl-seryl-aspartyl-lysyl-proline. *J Clin Invest,* 1996 Feb. 1; 97(3):588.
11. Winbury M M, Gabel L P. Effect of nitrates on nutritional circulation of heart and hindlimb. Am J Physiol. 1967 May; 212(5):1062-6.
12. Cohn J N, Johnson G, Ziesche S et al, A comparision of enalpril with hydralazine-isosorbide dintrate in the treatment of chronic congestive heart failure. *N Engl J Med;* 325:303-310.
13. Brater D C, Diuretic Therapy, N Engl. J Med, 1998; 339: 387-395.
14. Weiner D. A, Ca antagonists in the treatment of ischemic heart disease: Angina pectoris, *Coron Artery Dis,* 5:14-20, 1994.
15. Psaty M. D, Heckbert S. R, Koepsell M. D et al, The risk of myocardial infarction associated with antihypertensive drug therapies, *JAMA,* 274 (8): 620-625, 1995.
16. Quyyumi A. A, Wrigh C, Mcckus L, Fox K. M, Effect of partiaql agonist activity in beta-blockers in severe angina pectoris; α double blind comparision of pindolol and atenolol, *Br Med J,* 289: 951-953, 1984.
17. Goodfriend T. L, Elliott M. E, Can K. J, Angiotensin receptors and their antagonists, *New Eng J Med,* 334: 1649-1654, 1996.
18. Cushman D. W, Ondetti M. A, History of design of captopril and related inhibitors of angiotensin converting enzyme, Hypertension, 17:589-592, 1991.
19. Patchetl A. H, Hams E. W, Tristram E. W, A new class of angiotensin converting enzyme inhibitors, Nature, 288: 280-283; 1980.
20. Singhvi S. M, Duchin K. L, Morrison R. A et al., Distribution of fosinopril sodium in healthy subjects, Br. J.Clin.Pharmacol., 25:9-15, 1988.
21. Vasment D, Bender N, The renin-angiotensin system and ramipril:a new converting enzyme inhibitor, J.Cardiovas. Pharmacol., 14 (suppl 4): S46-S52; 1989.
22. Hodsman G P et al, Factors related to first dose hypotensive effect of captopril: prediction and treatment, BMJ, 286:832-834, 1983.
23. Gavras H. Gavras I, Angiotensin converting enzyme inhibitors: Properties and side effects, Hypertension, 11 (suppl II), 1137-1141, 1980.
24. Israili Z. H, Hall W. D, Cough and angioneurotic edema associated with angiotensin converting enzyme therapy, Ann Intern Med., 117: 234-242, 1992.
25. Antinios T. F. T, MacGregor G. A, Angiotensin converting enzyme inhibitors in hypertension, J. Hypertension, 13 (suppl 3), S11-S16, 1995.
26. DiBianco R, Adverse reactions with angiotensin converting enzyme inhibitors, Med Toxicol, 1:122-141, 1986.
27. Hodsman G P, Isles C G, Murray G D, Usherwood T P, Webb D J, Robertson J I. Factors related to first dose hypotensive effect of captopril: prediction and treatment. *Br Med J,* 1983 Mar. 12; 286(6368):832-4.
28. Hricik De et al, Captopril induced renal insufficiency in patients with bilateral renal artery stenosis or renal artery stenosis in a solitary kidney, *N Engl J Med,* 308:373-376, 1983
29. Warren S E, O'Connor D T, Hyperkalemia resulting from captopril administration *JAMA,* 1980; 244:2551-2552.
30. Beelay N, Peptidomimics and small-molecule drug design: towards improved bioavailability and in vivo stability, *TIBTECH,* 12:213-216; 1994.
31. Cheung H. S, Wang F. L, Ondetti M. A, Sabo F. E, Cushman D. W, Binding of peptide substrate and inhibitors of angiotensin converting enzyme, *J Biol Chem,* 255:401-407, 1980.
32. Furk A, Sebestyen F, Asgedam M, Dibo G, General method for rapid synthesis of multicomponent peptide system, *Int. J. Pept. Prot. Res.,* 37:487, 1991.
33. Beck-sickinger A. G, Jung G, Multiple peptide synthesis to peptide libraries. In: Jung G. ed; Combinatorial peptides and nonpeptide libraries. VCH Publishers, Germany, 1996
34. Elijovich F, Krakoff L R, Effect of converting enzyme inhibition on glucocorticocoid hypertension in the rat. *Am. J Physiol,* 238: H844, 1980.

The invention claimed is:
1. A peptidomimetic compound having the formula Xaa-$AA_1$-$AA_2$, wherein Xaa is a heterocyclic or unusual amino acid, AA₁ and AA₂ are amino acids, and the bond between Xaa and AA₁ is either C(O)—NH or CH₂—NH, wherein the peptidomimetic compound is selected from the group consisting of L-Abrine-Orn-Pro, 3-(3-thienyl)-L-alanine-Orn-Pro, 3-(2-furyl)-L-alanine-Orn-Pro, 2-Benzimidazoleacetic acid-Orn-Pro, 5-Hydroxytrytophan-Orn-Pro, Homotryptophan-Orn-Pro, Homophenyalanine-Orn-Pro, 1,2,3,4-tetrahydro isoquinoline-3-carboxylic acid-Orn-Pro, Azetidine-3-carboxylic acid-Orn-Pro, Cyclohexylalanine-Orn-Pro, 2-Oxo-4-phenyl-3-oxazolidine acetic acid-Orn-Pro, and 4-piperazine acetic acid-Orn-Pro.

2. A peptidomimetic compound having the general formula Xaa-AA₁-AA₂, where
Xaa is a heterocyclic or unusual amino acid;
AA₁ and AA₂ are amino acids; and
the bond between Xaa and AA₁ is either C(O)—NH or CH₂—NH,
wherein AA₁ is Ornithine, AA₂ is Proline and Xaa is L-Abrine.

3. A composition comprising the peptidomimetic compound according to claim 1, wherein the composition comprises a concentration of the peptidomimetic compound for 50% inhibition (IC₅₀) of angiotensin converting enzyme (ACE) activity.

4. The composition according to claim 3, wherein the composition comprises a dose of the peptidomimetic compound sufficient to block angiotensin converting enzyme ranging between 5-8 mg/kg of body weight of a mammal.

5. A process to synthesize the peptidomimetic compound of claim 1, comprising:
(a) synthesizing the dipeptide AA₁-AA₂ on a solid support;
(b) coupling the heterocyclic or unusual amino acid to the N-α terminal of the dipeptide;
(c) cleaving the synthesized peptidomimetic compound from the solid support; and
(d) purifying the peptidomimetic compound; thereby forming the peptidomimetic of claim 1.

6. A method for inhibiting an angiotensin converting enzyme in a mammal comprising administering the peptidomimetic compound of claim 1 to the mammal.

7. The method according to claim 6 wherein the peptidomimetic compound is administered to the mammal in a dose effective to block angiotensin converting enzyme in the mammal, said dose ranging between 5-8 mg/kg of body weight of the mammal.

8. A method of inhibiting angiotensin converting enzyme in a subject suffering from hypertension comprising administering to the subject a pharmaceutically effective amount of the peptidomimetic compound of claim 2 with a pharmaceutically effective carrier.

9. The method according to claim 8 wherein the subject is a mammal.

10. The method according to claim 8 wherein the subject is a human.

11. The method according to claim 8 wherein the peptidomimetic compound is administered to the subject in a dose which effectively blocks angiotensin converting enzyme in the subject, said dose ranging between 5-8 mg/kg of body weight of the subject.

* * * * *